(12) United States Patent
Yamashita et al.

(10) Patent No.: US 11,168,113 B2
(45) Date of Patent: *Nov. 9, 2021

(54) PEPTIDE AND USE THEREOF

(71) Applicants: SHIBAURA INSTITUTE OF TECHNOLOGY, Koto-ku (JP); JX NIPPON MINING & METALS CORPORATION, Tokyo (JP)

(72) Inventors: Mitsuo Yamashita, Tokyo (JP); Akira Miura, Hitachi (JP)

(73) Assignees: SHIBAURA INSTITUTE OF TECHNOLOGY, Tokyo (JP); JX NIPPON MINING & METALS CORPORATION, Tokyo (JP)

( * ) Notice: Subject to any disclaimer, the term of this patent is extended or adjusted under 35 U.S.C. 154(b) by 74 days.

This patent is subject to a terminal disclaimer.

(21) Appl. No.: 16/307,438

(22) PCT Filed: Jun. 6, 2017

(86) PCT No.: PCT/JP2017/021027
§ 371 (c)(1),
(2) Date: Dec. 5, 2018

(87) PCT Pub. No.: WO2017/213153
PCT Pub. Date: Dec. 14, 2017

(65) Prior Publication Data
US 2019/0345200 A1 Nov. 14, 2019

(30) Foreign Application Priority Data
Jun. 6, 2016 (JP) .............................. JP2016-112986

(51) Int. Cl.
| | | |
|---|---|---|
| C07K 7/08 | (2006.01) | |
| B01D 15/38 | (2006.01) | |
| B01D 21/00 | (2006.01) | |
| B01J 20/24 | (2006.01) | |
| B01J 20/28 | (2006.01) | |
| B01J 20/286 | (2006.01) | |
| C01G 39/06 | (2006.01) | |
| C22B 34/34 | (2006.01) | |

(52) U.S. Cl.
CPC ............ *C07K 7/08* (2013.01); *B01D 15/3823* (2013.01); *B01D 21/0084* (2013.01); *B01J 20/24* (2013.01); *B01J 20/286* (2013.01); *B01J 20/28016* (2013.01); *B01J 20/28052* (2013.01); *C01G 39/06* (2013.01); *C22B 34/34* (2013.01); *B01J 2220/52* (2013.01)

(58) Field of Classification Search
None
See application file for complete search history.

(56) References Cited

U.S. PATENT DOCUMENTS

| | | | |
|---|---|---|---|
| 10,954,531 B2 * | 3/2021 | Yamashita .............. | C07K 7/08 424/204.1 |
| 2019/0309325 A1 | 10/2019 | Yamashita et al. | |

FOREIGN PATENT DOCUMENTS

| | | |
|---|---|---|
| JP | 3277532 B2 | 4/2002 |
| JP | 2013-181021 A | 9/2013 |
| JP | 2014-188428 A | 10/2014 |
| JP | 2014-239678 A | 12/2014 |
| JP | 2015-224225 A | 12/2015 |
| JP | 2016-47810 A | 4/2016 |
| JP | 2016047810 * | 4/2016 |
| WO | WO 2013/154731 A1 | 10/2013 |

OTHER PUBLICATIONS

UniProtKB—AOA151Z8Q5, downloaded on Sep. 29, 2020 (Year: 2020).*
International Search Report for PCT/JP2017/021027 (PCT/ISA/210) dated Sep. 28, 2017.
Nishitani et al., "Molecular design of yeast cell surface for adsorption and recovery of molybdenum, one of rare metals", Applied Microbiology and Biotechnology, Springer, Berlin, DE, vol. 86, No. 2, Nov. 6, 2009, pp. 641-648, XP 019799867, ISSN: 1432-0614.
Written Opinion of the International Searching Authority for PCT/JP2017/021027 (PCT/ISA/237) dated Sep. 28, 2017.
XP-002773755, Database UniProt [Online], Jun. 26, 2013, retrieved from EBI accession No. UNIPROT:NODL24, Database accession No. NODL24 sequence, total of 2 pages.
XP-002773756, Database WPI, Week 201630, Thomson Scientific, London, GB; AN 2016-20758H, Apr. 7, 2016, total of 2 pages.
XP-002773757, Database WPI, Week 201504, Thomson Scientific, London, GB; AN 2015-00017S, Dec. 25, 2014, total of 2 pages.
XP-002773758, Database WPI, Week 201602, Thomson Scientific, London, GB; AN 2015-79741Q, Dec. 14, 2015, total of 2 pages.
XP-002773759, Database WPI, Week 201363, Thomson Scientific, London, GB; AN 2013-N18648, Sep. 12, 2013, total of 2 pages.

* cited by examiner

*Primary Examiner* — Sergio Coffa
(74) *Attorney, Agent, or Firm* — Birch, Stewart, Kolasch & Birch, LLP.

(57) ABSTRACT

(Technical problems to be solved) Providing a method for selecting an mineral of molybdenum. (Means for solving the problems) A peptide comprising an amino acids sequence according the following formula (1) and/or (2): (1) (ALRKNMD-FCPQSETGWHYIV)-(LIVFA)-(HPWRK)-(TSNQ)-(TSNQ)-(LIVFA)-(TSNQ)-(TSNQ)-(LIVFA)-(FYW)-(LIVFA)-(HPWRK) (2) (LIVFA)-(RHK)-(TSNQ)-(LIVFA)-(LIVFA)-(TSNQ)-(LIVFA)-(LIVFA)-(LIVFA)-(RHK)-(RHK)-(HPW) wherein one amino acid is respectively selected from each group defined by paired parentheses.

14 Claims, 4 Drawing Sheets
Specification includes a Sequence Listing.

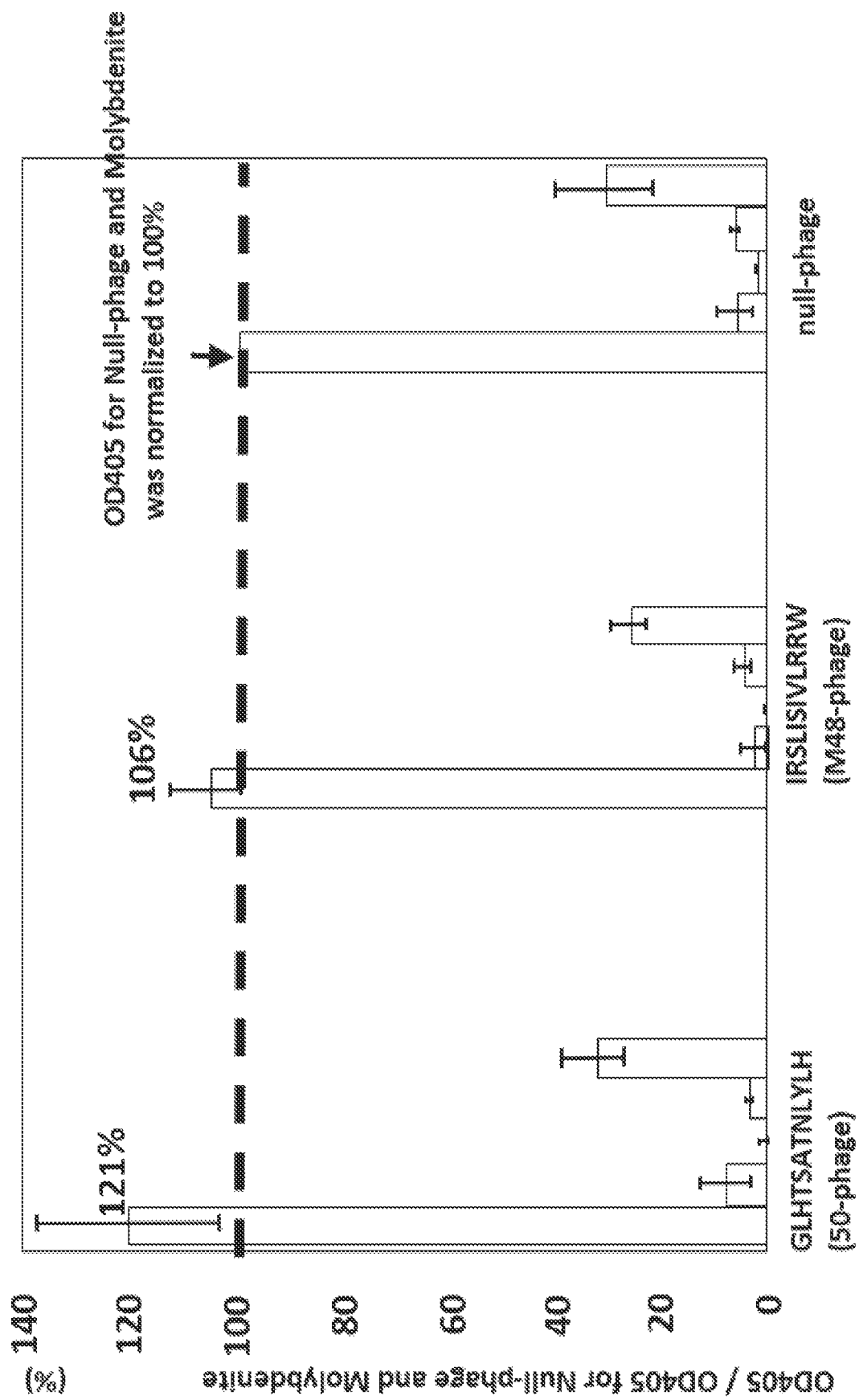
[Fig. 1]

[Fig. 2]
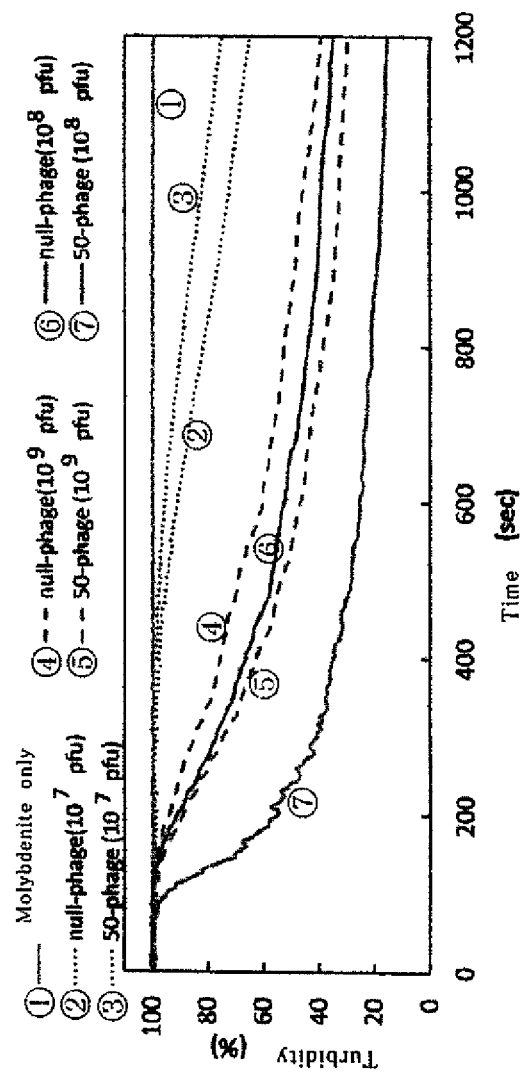

[Fig. 3]
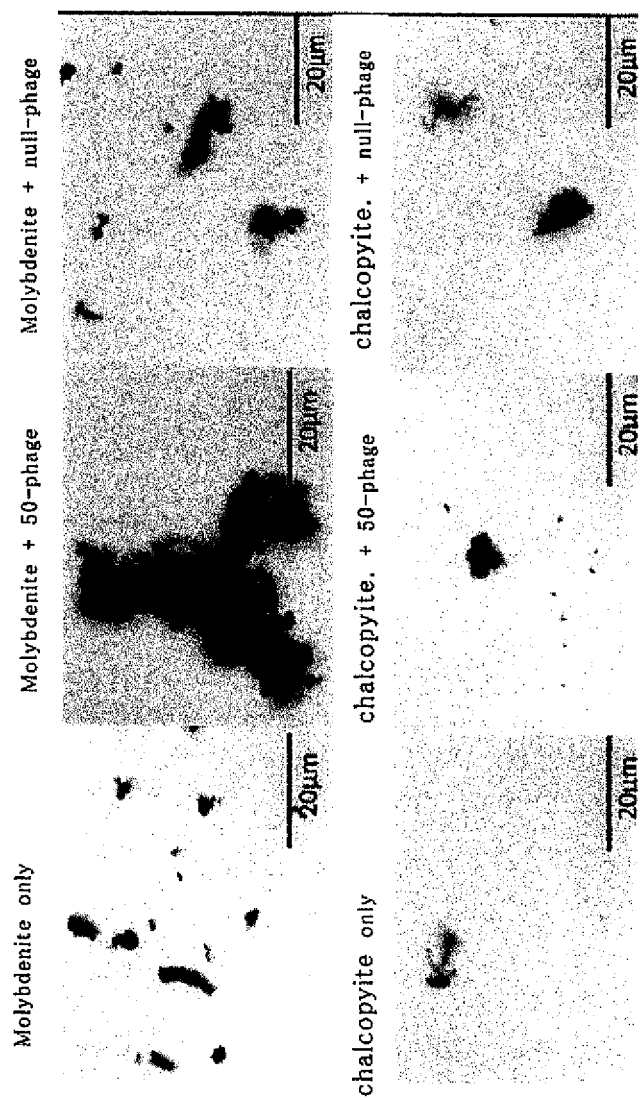

[Fig. 4]
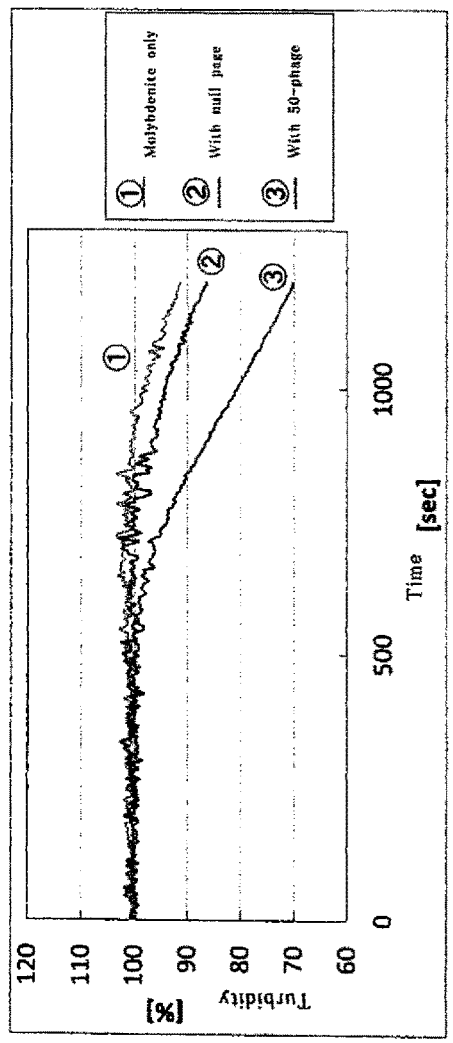
[Fig. 5]
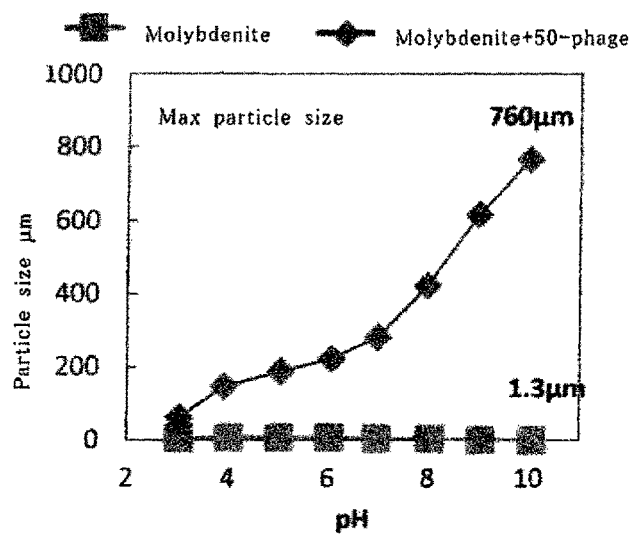

PEPTIDE AND USE THEREOF

TECHNICAL FIELD

Reference to Sequence Listing Submitted Via Efs-Web

This application includes an electronically submitted sequence listing in .txt format. The .txt file contains a sequence listing entitled "2021-05-18 5526-0153PUS1 ST25.txt" created on Jun. 15, 2021 and is 1590 bytes in size. The sequence listing contained in this .txt file is part of the specification and is hereby incorporated by reference herein in its entirety.

The present invention is related to a novel peptide and use thereof. More particularly, the present invention is related to a novel peptide specifically biding to a certain element and use thereof.

BACKGROUND ART

Molybdenum is a valuable chemical element, which is used for such as an ingredient of an alloy of special steel, catalyst for purifying oil, and lubricant. Molybdenum often exists in Porphyry copper deposit etc., in which copper sulfide ores exist in accompany with molybdenite as an sulfide mineral, which is recovered as molybdenum concentrate. The molybdenum concentrate mined from Porphyry copper deposit is recovered as byproduct of froth floatation in the process of concentrating and/or refining copper sulfide mineral. The molybdenite tends to float, and thus it can easily float by adding a frother in addition to a collector such as kerosene and diesel oil. However, since an copper sulfide mineral, which is accompanied with molybdenite, also tends to float, it is required to add cyanide and/or sodium hydrogen sulfide for the purpose of suppressing float of copper sulfide minerals.

However, the drawbacks of these are: that cyanide has a risk of environmental pollution by its toxicity; and that the presence of sodium hydrogen sulfide leads to production of hydrogen sulfide when mineral slurry is acidic.

Patent document 1 discloses a method for refining molybdenum mineral without use or occurrence of toxic substances, in which oxidation of ozone is applied. Patent document 2 discloses a method for utilizing plasma irradiation. Patent document 3 discloses an amino acid is supported by a carrier to recover a molybdenum compound.

CITATION LIST

Patent Literature

PTL 1: Japanese Patent No 3277532
PTL 2: Japanese Patent Publication No 2014-188428
PTL 3: Japanese Patent Publication No 2015-224225

SUMMARY OF INVENTION

Technical Problem

In the above disclosed methods, specialized devices are required for utilizing ozone or irradiating plasma, both of which are impractical, and thus neither of them has not been realized yet.

An object of the present invention is to provide novel methods for isolating a substance containing molybdenum.

Solution to Problem

In light of the above object, the present inventors have studied intensively and found that certain peptides and phages having certain peptides can selectively bind to molybdenite. Moreover, these peptides are valuable for refining molybdenite.

On the basis of the above discovery, in one aspect, the present invention includes the following inventions.

(Invention 1)

A peptide comprising an amino acids sequence according the following formula (1) and/or (2):

(1)
(A, L, R, K, N, M, D, F, C, P, Q, S, E, T, G, W, H, Y, I, V)-(L, I, V, F, A)-(H, P, W, R, K)-(T, S, N, Q)-(T, S, N, Q)-(L, I, V, F, A)-(T, S, N, Q)-(T, S, N, Q)-(L, I, V, F, A)-(F, Y, W)-(L, I, V, F, A)-(H, P, W, R, K)

(2)
(L, I, V, F, A)-(R, H, K)-(T, S, N, Q)-(L, I, V, F, A)-(L, I, V, F, A)-(T, S, N, Q)-(L, I, V, F, A)-(L, I, V, F, A)-(L, I, V, F, A)-(R, H, K)-(R, H, K)-(H, P, W)

wherein one amino acid is respectively selected from each group defined by paired parentheses.

(Invention 2)

A peptide comprising at least any one of the following sequences (A) and (B):

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp (Invention 3)

A peptide according to any one of the following sequences (A) and (B):

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp (Invention 4)

A peptide comprising a sequence which is at least 90% identical to any one of the following sequences (A) and (B):

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp (Invention 5)

A peptide comprising a sequence which is at least 95% identical to any one of the following sequences (A) and (B):

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp (Invention 6)
A peptide comprising a sequence which is at least 98% identical to any one of the following sequences (A) and (B):

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp (Invention 7)
A peptide comprising a sequence derived from at least any one of the following sequences (A) and (B) by deleting, replacing, and/or adding 1-5 amino acid:

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp (Invention 8)
A composition for selecting a mineral, the composition comprising the peptide of any one of Inventions 1-7.

(Invention 9)
A nucleic acid encoding the peptide of any one of Inventions 1-7.

(Invention 10)
A nucleic acid comprising a sequence which is at least 90% identical to a nucleic acid sequence encoding to the peptide of any one of Inventions 1-7.

(Invention 11)
A nucleic acid being capable of hybridizing under a stringent condition with a sequence being complimentary to a nucleic acid encoding the peptide of any one of Inventions 1-7.

(Invention 12)
A microorganism comprising on its surface the peptide of any one of Inventions 1-7.

(Invention 13)
A microorganism comprising the nucleic acid of any one of Inventions 9-11.

(Invention 14)
A particle comprising on its surface the peptide of any one of Inventions 1-7.

(Invention 15)
A purification column comprising the peptide of any one of Inventions 1-7.

(Invention 16)
A reagent for use of floatation comprising the peptide of any one of Inventions 1-7.

(Invention 17)
A method for isolating molybdenum mineral, the method comprising using the peptide of any one of Inventions 1-7.

(Invention 18)
A method for selecting an mineral, the method comprising using the peptide of any one of Inventions 1-7 or the composition of Invention 8.

(Invention 19)
The method of Invention 18, wherein the mineral is molybdenite.

(Invention 20)
The method of Invention 18 or 19, the method comprising:
adding a microorganism into mineral dispersion, wherein the microorganism comprises the peptide on its surface;
aggregating and precipitating the mineral; and
recovering the aggregated and precipitated mineral.

(Invention 21)
The method of Invention 18 or 19, the method comprising:
affixing the peptide to a carrier;
introducing the carrier into a column for chromatography; and
passing mineral dispersion through the column.

(Invention 22)
The method of Invention 18 or 19, the method comprising:
affixing the peptide to a particle; and
introducing the particle into mineral dispersion.

(Invention 23)
The method of Invention 18 or 19, the method comprising froth floating with use of the peptide.

(Invention 24)
The method of any one of Inventions 18-23, wherein pH of the mineral dispersion is 4 or more.

(Invention 25)
The method of any one of Inventions 18-23, wherein pH of the mineral dispersion is 7 or more.

Advantageous Effects of Invention

In one aspect, the present invention utilizes a peptide. Thereby, it does not require a large scale of devices comparing to conventional techniques. Also, it does not require using toxic compounds or any compounds that have a risk of producing toxic compounds, such as cyanide and sodium hydrogen sulfide. Thus, safe isolation is possible.

Furthermore, the peptides according to the present invention enable to isolate efficiently. Moreover, a mineral of interest can be selectively isolated. In addition, in one aspect, the peptides according to the present invention can be used under environment of certain pH range. Thereby, binding to molybdenum (and its aggregation) of a mineral can be enhanced more.

BRIEF DESCRIPTION OF DRAWINGS

FIG. 1 (SEQ ID NOS: 1 and 2) is a graph showing that the peptides according to one embodiment of the present invention can selectively bind to a certain mineral. Five bars in each group represent, in the order from left to right, OD405 of molybdenite, elemental sulfur, chalcopyrite, enargite, and pyrite respectively.

FIG. 2 is a graph showing that turbidity changes when molybdenite is precipitated with use of 50-phage etc. according to one embodiment of the present invention.

FIG. 3 is a photograph showing a size of particles when molybdenite is precipitated with use of 50-phage etc. according to one embodiment of the present invention.

FIG. 4 is a graph showing that turbidity changes when molybdenite is precipitated with use of 50-phage etc. according to one embodiment of the present invention.

FIG. 5 is a graph showing that a maximum size of particle changes when molybdenite is precipitated with use of 50-phage etc. according to one embodiment of the present invention. This change depends on pH.

DESCRIPTION OF EMBODIMENTS

Now, for the purpose of enhancing the understanding of the present invention, more specified embodiments are described hereinafter, which are not intended to limit the scope of the present invention.

1. Applicable Substances

In one embodiment, the present invention can be applicable to a method for isolating certain substances. The certain substances may include a substance containing molybdenum. More specifically, in one embodiment, the present invention can be applicable to a method for isolating a mineral containing molybdenum. A mineral containing molybdenum may include molybdenite, wulfenite, powellite, ferrimolybdite etc. A typical example for a mineral containing molybdenum includes molybdenite since it is commonly mined.

2. Peptide

For the purpose of isolating the substances described above, in one embodiment of the present invention, a peptide can be used. More specifically, a peptide can be used that includes an amino acids sequence according the following formula (1) and/or (2). Additionally, certain number of amino acid can be added in their N terminal and/or C terminal. The certain number may fall within numerical range defined by two numbers selected from 1, 2, 3, 4, 5, 6, 7, 8, 9, 10, 15, and 20 (e.g., from 1 to 10, or from 5 to 20).

(1)
(A, L, R, K, N, M, D, F, C, P, Q, S, E, T, G, W, H, Y, I, V)-(L, I, V, F, A)-(H, P, W, R, K)-(T, S, N, Q)-(T, S, N, Q)-(L, I, V, F, A)-(T, S, N, Q)-(T, S, N, Q)-(L, I, V, F, A)-(F, Y, W)-(L, I, V, F, A)-(H, P, W, R, K)

(2)
(L, I, V, F, A)-(R, H, K)-(T, S, N, Q)-(L, I, V, F, A)-(L, I, V, F, A)-(T, S, N, Q)-(L, I, V, F, A)-(L, I, V, F, A)-(L, I, V, F, A)-(R, H, K)-(R, H, K)-(H, P, W)

(wherein one amino acid is respectively selected from each group defined by paired parentheses)

The working examples described hereinafter show the peptides according to the following amino acid sequences were used to isolate molybdenite.

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp

The above amino acid sequences of (1) and (2) and the above amino acid sequences of (A) and (B) correspond as follows.

TABLE 1

| | (A) | (1) |
|---|---|---|
| 1 | Gly | A L R K N M D F C P Q S E T G W H Y I V |
| 2 | Leu | L I V F A |
| 3 | His | H P W R K |
| 4 | Thr | T S N Q |
| 5 | Ser | T S N Q |
| 6 | Ala | L I V F A |
| 7 | Thr | T S N Q |
| 8 | Asn | T S N Q |
| 9 | Leu | L I V F A |
| 10 | Tyr | F Y W |
| 11 | Leu | L I V F A |
| 12 | His | H P W R K |

TABLE 2

| | (B) | (2) |
|---|---|---|
| 1 | Ile | L I V F A |
| 2 | Arg | R H K |
| 3 | Ser | T S N Q |
| 4 | Leu | L I V F A |
| 5 | Ile | L I V F A |
| 6 | Ser | T S N Q |
| 7 | Ile | L I V F A |
| 8 | Val | L I V F A |
| 9 | Leu | L I V F A |
| 10 | Arg | R H K |
| 11 | Arg | R H K |
| 12 | Trp | H P W |

As shown in Table 1, the first amino acid in the sequence (A) is glycine. Since the residue of glycine is (—H), it is not likely that the residue itself contributes to certain function. Thus, even if replacing glycine with the other natural amino acids, the peptide will retain same or similar property.

The second amino acid in the sequence (A) is leucine, which is a hydrophobic amino acid. Thus, even if replacing with isoleucine, valine, phenylalanine, alanine, etc., which are also hydrophobic, the peptide will retain same or similar property.

The third amino acid in the sequence (A) is histidine. Histidine has heterocyclic ring in its residue. Thus, even if replacing with tryptophan or proline, which also have heterocyclic ring in their residue, the peptide will retain same or similar property. Furthermore, histidine is polar-charged (basic) amino acid. Thus, even if replacing with arginine or lysine, which are also polar-charged (basic) amino acids, the peptide will retain same or similar property.

The 4th and 5th amino acids in the sequence (A) are threonine and serine respectively. These are a polar non-charged amino acid. Thus, even if replacing with threonine, serine, asparagine, or glutamine, which are also polar non-charged amino acids, the peptide will retain same or similar property.

The 10th amino acid in the sequence (A) is tyrosine, which is an aromatic amino acid. Thus, even if replacing with tryptophan or phenylalanine, which are also aromatic amino acids, the peptide will retain same or similar property.

The second amino acid in the sequence (B) is arginine, which has a basic residue. Thus, even if replacing with lysine or histidine, which are also basic amino acids, the peptide will retain same or similar property.

As similar to the above, the other amino acids can be replaced on the basis of the same or similar point of view (e.g., hydrophobic-hydrophilic, acidic-neutral-basic, common functional group, etc.).

In one embodiment, the present invention encompasses the peptides including at least any one of the following sequences.

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp

Additionally, an arbitrary number of amino acid can be added in their N terminal and/or C terminal. Typically, the arbitrary number may fall within numerical range defined by two numbers selected from 1, 2, 3, 4, 5, 6, 7, 8, 9, 10, 15, and 20 (e.g., from 1 to 10, or from 5 to 20).

In one embodiment, the present invention encompasses the peptides represented by any one of the following 12-amino acid sequences.

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp

Regarding to the above amino acid sequences (A) and (B), even if making a slight modification (e.g., insertion, replacement, and/or addition of amino acid), the modified peptide will retain property that is the same as or similar to those of amino acids sequences (A) and/or (B). For example, a peptide or a peptide including a sequence which is 66% or more, 75% or more, 83% or more, 90% or more, 95% or more, 98% or more, or 99% or more identical to the amino acids sequences (A) and/or (B), will also retain the same or similar property.

A numerical value for sequence similarity can be calculated by technique known in the art. For example, the value may be calculated based on a value derived by Blastp, which is used for homology search of amino acids (or protein) and is provided by BLAST (Trademark)

In one embodiment, the present invention encompasses a peptide comprising a sequence derived from at least any one of the following sequences (A) and (B) by deleting, replacing, and/or adding 1-5 amino acid, typically, by deleting, replacing, and/or adding 4 or less, 3 or less, or 2 or less amino acids.

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp

In one embodiment, the present invention encompasses a composition containing at least any one of the above peptides. In other words, not only the above peptides, but also a composition containing at least any one of the above peptides together with other ingredients can achieve the same or similar functions. The composition may contain arbitrary ingredients (e.g., buffer, NaCl, sugar etc.) on the conditions that they do not deteriorate the functions of the above peptides.

4. Nucleic Acid Encoding Peptide

In one embodiment, the present invention encompasses a nucleic acid encoding at least any one of the above peptides. The nucleic acid may be DNA or RNA. In one embodiment, the present invention encompasses a nucleic acid having a sequence being complimentary to a sense strand encoding at least any one of the above peptides.

In one embodiment, the present invention encompasses a nucleic acid comprising a sequence which is at least 80% or more, 85% or more, 90% or more, 95% or more, or 98% or more identical to a nucleic acid sequence encoding to at least any one of the above peptides. As similar to the case of amino acids sequence, a numerical value for sequence similarity can be calculated by technique known in the art. For example, the value may be calculated based on a value derived from a search result by Blastn, which is provided by BLAST Moreover, in one embodiment, the present invention encompasses a nucleic acid being capable of hybridizing with a sequence being complimentary to sense strand of a nucleic acid encoding at least any one of the above peptides. More specifically, the present invention encompasses the nucleic acid being capable of hybridizing under a stringent condition. The stringent condition may be a condition known in the art. For example, it may be a condition that is disclosed in Japanese patent publication No. 2015-023831. More specifically, it may be judged through the following procedure: using a filter in which DNA is fixed; hybridization in the presence of 0.7-1.0 M of NaCl under the temperature 65 degree Celsius; and washing a filter at the temperature of 65 degree Celsius, by 0.1-2×SSC (saline-sodium citrate) solution (1×SSC solution contains 150 mM NaCl, 15 mM Sodium citrate).

Any of the above described nucleic acids are usable for preparing a peptide of interest through genetic engineering technique. For example, any one or more of the above described nucleic acids may be introduced into expression vector to express a peptide of interest in a large scale. Alternatively, a phage having a peptide of interest on its surface may be prepared through a phage display method described hereinafter.

5. Usage of Peptide and/or Nucleic Acid

The above described peptides and/or nucleic acids may be applicable in various ways.

5-1. Microorganism

For example, utilizing genetic engineering technique (e.g., introducing at least any one of the above nucleic acids into genome of a microorganism), the microorganism may produce a peptide of interest in a large scale. Alternatively, expressing a peptide of interest in a surface of a microorganism, a substance of interest may be isolated with use of the microorganism. The term "microorganism" described herein includes organism belonging to fungi, monera, or protist of five-kingdom system. Also, the term "microorganism" described herein includes virus, though it does not belong to organism in a strict classification. Typically, fungi, bacteria, or virus may be used. Preferably, a microorganism may be used in which genetic engineering procedure is established (e.g., yeast, *E. coli, lactobacillus*, a bacteriophage). In one embodiment, the present invention encompasses such microorganisms.

5-2. Particle

In one embodiment, the present invention encompasses a particle having a peptide on its surface. The peptide may be any one of the above described peptides. Moreover, an example for a particle may include beads (e.g., magnetic beads, glass beads, high-molecular beads etc.), and a carrier and etc. A size of a particle is not limited, and may be adjusted depending on its usage. A peptide may be bound to a surface of a particle by technique known in the art.

In one embodiment of the present invention, a substance of interest may be isolated with use of a particle having at least any one of the above peptides on its surface. For example, via the method described hereinafter, a substance of interest may be bound to the peptides and precipitated to be isolated.

5-3. Column for Purification

A substance of interest may be isolated via column chromatography. Column chromatography relies on property where a column (or functional groups on inner surface of column) selectively binds to certain substance. In one embodiment of the present invention, the above described peptides can be affixed to a carrier and then the carrier may be introduced into a column. Utilizing such a column, a substance of interest may be isolated.

5-4. Collector for Froth Flotation

Froth flotation is a method for separation by trapping particles via bubble. In this method, a collector may be used. In one embodiment of the present invention, if the above peptides are easily trapped by bubble, the peptides themselves may be used as a collector. Alternatively, the peptides may be bound to a collector or a frother known in the art, to enhance the trap by bubble. Thereby, a substance of interest may be trapped by bubble and consequently be isolated.

6. Embodiment for Application (Methods for Isolation)

Now methods for the above application are described hereinafter.

6-1. Substances to be Isolated

The above described embodiments for application are related to isolating a certain substance. In these embodiments, a substance to be isolated may be molybdenum. For example, the above described molybdenum-containing mineral (e.g., molybdenite) may be isolated.

6-2. A Method with Use of a Microorganism

In one embodiment of the present invention, using a microorganism, a substance (specifically, molybdenum-containing mineral, more specifically, molybdenite) may be isolated. Regarding to a microorganism, any of the above described microorganisms may be used. Typically, a bacteriophage may be used.

Regarding to procedure, initially, by technique of genetic engineering known in the art, a nucleic acid sequence encoding the above described peptides may be introduced into a microorganism, to express them on the surface of the microorganism. Then, the microorganism may be introduced into mineral dispersion (liquid in which mineral particles are dispersed).

An amount of introduction for a microorganism may be appropriately adjusted by considering certain conditions such as an amount of mineral dispersing in liquid. For example of a phage, in relative to 3 g/L of mineral particle, the amount of a phage may be $0.5 \times 10^{\wedge}8$ pfu/mL-$5 \times 10^{\wedge}8$ pfu/mL, more preferably, $0.6 \times 10^{\wedge}8$ pfu/mL-$1.5 \times 10^{\wedge}8$ pfu/mL. Alternatively, in relative to 10 g/L of mineral particle, the amount of a phage may be $0.5 \times 10^{\wedge}9$ pfu/mL-$5 \times 10^{\wedge}9$ pfu/mL, more preferably, $0.6 \times 10^{\wedge}9$ pfu/mL-$1.5 \times 10^{\wedge}9$ pfu/mL.

Alternatively, the ratio of an amount of a phage (pfu/mL)/an amount of mineral (g/L) may be $0.13 \times 10^{\wedge}8$-$5 \times 10^{\wedge}8$, more preferably $0.33 \times 10^{\wedge}8$-$1 \times 10^{\wedge}8$.

Introducing a microorganism and then leaving a microorganism for a while, peptides on the surface of the microorganism bind to mineral particles to be aggregated and then to be precipitated. After this, the precipitated ore on the bottom may be recovered.

6-3. A Method for Isolating by Column Chromatography

In one embodiment of the present invention, via column chromatography, a substance (specifically, molybdenum-containing mineral, more specifically, molybdenite) may be isolated. In this procedure, initially, at least any one of the above described peptides is affixed to a carrier by technique known in the art. Then, the carrier may be introduced into column for purification. After preparing the column, liquid in which a substance disperses is passed through the column. Then the substance binds to inside of the column, and/or elution of the substance is delayed. Thereby, the substance of interest may be isolated.

6-4. A Method for Isolating by a Particle

In one embodiment of the present invention, using a particle, a substance (specifically, molybdenum-containing mineral, more specifically, molybdenite) may be isolated. Initially, the above described peptides may be affixed to the surface of the particle by technique known in the art. Then, the particle may be introduced into mineral dispersion (liquid in which mineral particles are dispersed). Introducing the peptide-bound particle and then leaving it for a while, peptides on the surface of the particle bind to mineral particles to be aggregated and then to be precipitated. After this, the precipitated mineral on the bottom may be recovered. Alternatively, a particle may be a magnetic bead, and without waiting precipitation, mineral particle may be recovered by magnetic power.

6-5. A Method for Froth Flotation

In one embodiment of the present invention, using a collector and/or a frother, a substance (specifically, molybdenum-containing mineral, more specifically, molybdenite) may be isolated. Specifically, a collector and/or a frother are bound to the above described peptides by technique known in the art. Then, the bound collector and/or frother is introduced into solution to be agitate (other agent may be introduced appropriately), and to form bubble. After this, mineral particles are introduced to be trapped by the bubble. Thereby, mineral particles may be recovered. Alternatively, a peptide itself may be used as a collector.

7. Selectivity for Biding to Mineral

The above described peptides have a feature of selectivity that they are capable of strongly binding to a certain ore, but do not bind to other minerals. More specifically, they are capable of strongly binding to a molybdenum-containing mineral (e.g., molybdenite), but do not bind to other minerals such as elemental sulfur, chalcopyrite, enargite, pyrite (alternatively, are capable of biding to other minerals with significantly less strength comparing to those of a molybdenum-containing mineral). Thus, even if it is a mixture of a molybdenum-containing mineral and other minerals, a molybdenum-containing mineral may be isolated by the above methods.

8. pH Dependency

In the procedure of binding the above described peptides to a molybdenum-containing mineral (e.g., molybdenite), adjusting pH of liquid to certain range can enhance binding (and aggregation). Specifically, as pH increases, maximum size of particles in particle distribution of liquid can increase. For example, within the pH range from 4 to 12, preferably within the pH range 5 or more, maximum size of particles can increase.

9. A Method for Preparing Peptide

The above described peptides may be prepared in various ways. DNA encoding at least any one of the above described peptides may be introduced into expression vector, and the vector may be introduced into a microorganism etc., to express the peptides in a large scale to be recovered.

Alternatively, in case of preparing a phage (e.g., M13-phage) having at least any one of the above described peptides on its surface, a phage display method may be available. A microorganism having a peptide of interest on its surface may be prepared by genetic engineering technique known in the art.

EXAMPLES

Now, via the following working examples, the above described embodiments of the present invention are described more specifically, although the scope of the present invention is not limited to the following working examples.

(Example 1) Selection of a Molybdenite-Adsorbing Phage Via a Phage Display Method For the purpose of screening peptides that are able to adsorb molybdenite, a phage display method was performed. Specifically, M13 bacteriophage library was constructed, in which peptides with 12 amino acids were randomly bound to phages. Using this library, molybdenite that was ground to the particle size of 75 micrometer or less was contacted with the library. Then, only bacteriophages that bound to molybdenite were recovered, and E. coli was infected with the recovered phages to grow the phages again. After that, the phages were contacted with molybdenite again, and only the adsorbed phages were recovered. These operations of adsorbing and recovering (panning) were repeated certain times. DNA sequences of the selected phages were analyzed to identify amino acids sequences binding to the phages.

At the first screening, a pulp density of the contacted molybdenite was 300 ppm and the panning was repeated 5 times. At the second screening, a pulp density of molybdenite was 3000 ppm, and the panning was repeated 4 times. DNA sequences for the resultant phages were analyzed and the phages having peptide according to the following amino acids sequences (A) and (B) were identified:

(A)
(SEQ ID NO: 1)
Gly-Leu-His-Thr-Ser-Ala-Thr-Asn-Leu-Tyr-Leu-His (B)
(SEQ ID NO: 2)
Ile-Arg-Ser-Leu-Ile-Ser-Ile-Val-Leu-Arg-Arg-Trp

Hereinafter, a phage being bound to the peptide (A) is referred to as 50-phage, and a phage being bound to the peptide (B) is referred to as M48-phage.

(Example 2) ELISA Analysis for Phages being Capable of Binding to Molybdenite

Using molybdenite and 50-phage and M48-phage that were screened in Example 1, an amount of binding were measured by ELISA method (Enzyme-Linked Immunosorbent Assay). Specifically, 3000 mg/L of molybdenite were suspended and then aliquoted to each well of 96-well microplate. Each phage was added into each well, and unbound phages were washed out. After that, anti M13-phage antibody conjugated with an enzyme (peroxidase) was added and then unbound anti-phage antibodies were washed out. Next, 2,2'-azino-bis (3-ethylbenzothiazoline-6-sulphonic acid) diammonium salt (ABTS), which is the substrate for the enzyme, was added. Bluecolored samples resulting from digestion of ABTS were analyzed by a microplate reader with the wave length of 405 nm. Furthermore, the same procedure was performed with the replacement with the other minerals (elemental sulfur, chalcopyrite, enargite, and pyrite).

FIG. 1 shows a ratio of absorbance. Specifically, the absorbance of ELISA analysis under the conditions that M13-phage not having the peptides (null-phage) was contacted with molybdenite was deemed to be 100% (i.e., reference absorbance). On the basis of the reference absorbance, the ratio of the amounts of absorbance for each mineral and each phage having each peptide were calculated (that is, a ratio of the amount of binding by "phage having peptide" to each mineral to the amount of binding by "null-phage" to molybdenite). As shown in FIG. 1, the amount of binding by 50-phage to molybdenite was larger by 121% in relative to the case where null-phage was contacted with molybdenite. The amount of binding for M48-phage was 106%. Further, the amounts of binding by 50-phage and M48-phage to the other minerals (elemental sulfur, chalcopyrite, enargite, and pyrite) were significantly lower than those of molybdenite. Comparing to the amount of binding by null-phage, their amount of binding did not significantly increase. Thus, it was shown that both phages (more specifically, the peptides expressed on the surfaces of the both phages) specifically bind to molybdenite (Example 3) Measurement for Precipitation Rate in the Case of Molybdenite with a Density of 3 g/L and Observation by a Microscope Under the conditions of the temperature of 30 degree Celsius, molybdenite with the particle size being 75 micrometer or less was suspended in water such that a pulp density was 3 g/L. Each of 50-phage and null-phage was added to the suspension such that each density was 10^7-10^9 pfu/ml. Then, turbidity in the upper portion of the suspension was measured with a spectrophotometer (wave length 660 nm) every 5 second after adding the phages. A change of the turbidity is shown in FIG. 2 (the turbidity at the time of adding the phages (0 second), was deemed to be 100%). As a result, when 50-phage was added with the density of 10^8 pfu/ml, the turbidity rapidly decreased, which demonstrates that the particles of molybdenite rapidly precipitated. Furthermore, the particles of molybdenite was observed by an optical microscope on the same conditions (FIG. 3), demonstrating that when 50-phage was added to molybdenite, the particles of molybdenite aggregated more significantly. These results indicate the possibility that molybdenite can be selectively isolated and recovered by adding 50-phage to suspension of molybdenite with an appropriate density.

(Example 4) Measurement of the Precipitation Speed and Observation by Microscope when Adding 50-Phage A precipitation rate after adding 50-phage was measured in the same manner as those of Example 3 except for the pulp density for molybdenite, which was 10 g/L. The result is shown in FIG. 4. On the conditions that a pulp density for molybdenite was 10 g/L and a density of 50-phage was 10^9 pfu/ml, it was shown that molybdenite significantly precipitated.

(Example 5) a Change of Maximum Particle Size when Adding 50-Phage and its pH Dependency Under the conditions of the temperature 30 degree Celsius, molybdenite with the particle size being 75 micrometer or less was suspended in water such that a pulp density was 10 g/L. The suspension was added with 50-phage such that a density of 50-phage is 10^9 pfu/ml. Then, pH of the suspension was adjusted to predetermined value with use of NaOH and HCl. A particle size was measured by the instruments, AcoustoSizerIIx (Kyowa Interface Science Co., Ltd.). The result was shown in FIG. 5. It was shown that as pH increased, a maximum particle size also increased. Especially in the case of pH being 4 or more, comparing to the case where only molybdenite was contained, adding 50-phage significantly increased a maximum particle size.

The invention claimed is:

1. A composition for selecting a mineral, the composition comprising a peptide, wherein the peptide comprises SEQ ID NO: 3.

2. The composition of claim 1, wherein the peptide comprises SEQ ID NO: 2.

3. The composition of claim 1, wherein the peptide consists of SEQ ID NO: 2.

4. The composition of claim 1, wherein the peptide comprises a sequence which is at least 90% identical to SEQ ID NO: 2.

5. A composition for selecting a mineral, the composition comprising a peptide consisting of a sequence derived from SEQ ID NO: 2 by deleting, replacing, and/or adding 1-2 amino acid.

6. A particle comprising on its surface the peptide of claim 1.

7. A purification column comprising the peptide of claim 1.

8. A reagent for use of floatation comprising the peptide of claim 1.

9. A method for selecting a mineral, the method comprising: adding a microorganism into mineral dispersion, wherein the microorganism comprises the peptide of claim 1 on its surface; aggregating and precipitating the mineral; and recovering the aggregated and precipitated mineral.

10. The method of claim 9, wherein the mineral is molybdenite.

11. A method for selecting a mineral, the method comprising: affixing the peptide of claim 1 to a carrier; introducing the carrier into a column for chromatography; and passing mineral dispersion through the column.

12. A method for selecting a mineral, the method comprising: affixing the peptide of claim 1 to a particle; and introducing the particle into mineral dispersion.

13. The method of claim 12, wherein pH of the mineral dispersion is 4 or more.

14. The method of claim 12, wherein pH of the mineral dispersion is 7 or more.

* * * * *

```
                        SEQUENCE LISTING

<160> NUMBER OF SEQ ID NOS: 3

<210> SEQ ID NO 1
   <211> LENGTH: 12
   <212> TYPE: PRT
   <213> ORGANISM: Artificial Sequence
   <220> FEATURE:
   <223> OTHER INFORMATION: Ramdomly synthesized peptide

<400> SEQUENCE: 1

Gly Leu His Thr Ser Ala Thr Asn Leu Tyr Leu His
   1               5                   10

<210> SEQ ID NO 2
   <211> LENGTH: 12
   <212> TYPE: PRT
   <213> ORGANISM: Artificial Sequence
   <220> FEATURE:
   <223> OTHER INFORMATION: Randomly synthesized peptide

<400> SEQUENCE: 2

Ile Arg Ser Leu Ile Ser Ile Val Leu Arg Arg Trp
   1               5                   10

<210> SEQ ID NO 3
   <211> LENGTH: 12
   <212> TYPE: PRT
   <213> ORGANISM: Artificial Sequence
   <220> FEATURE:
   <223> OTHER INFORMATION: Synthetic
   <220> FEATURE:
   <221> NAME/KEY: misc_feature
   <222> LOCATION: (1)..(1)
   <223> OTHER INFORMATION: X can be L, I, V, or A
   <220> FEATURE:
   <221> NAME/KEY: misc_feature
   <222> LOCATION: (3)..(3)
   <223> OTHER INFORMATION: X can be T, or S
   <220> FEATURE:
   <221> NAME/KEY: misc_feature
   <222> LOCATION: (4)..(4)
   <223> OTHER INFORMATION: X can be L, I, V, or A
   <220> FEATURE:
   <221> NAME/KEY: misc_feature
   <222> LOCATION: (5)..(5)
   <223> OTHER INFORMATION: X can be L, I, V, or A
   <220> FEATURE:
   <221> NAME/KEY: misc_feature
   <222> LOCATION: (6)..(6)
   <223> OTHER INFORMATION: X can be T, S
   <220> FEATURE:
   <221> NAME/KEY: misc_feature
   <222> LOCATION: (7)..(7)
```

```
<223> OTHER INFORMATION: X can be L, I, V, or A
<220> FEATURE:
<221> NAME/KEY: misc_feature
<222> LOCATION: (8)..(8)
<223> OTHER INFORMATION: X can be L, I, V, or A
<220> FEATURE:
<221> NAME/KEY: misc_feature
<222> LOCATION: (9)..(9)
<223> OTHER INFORMATION: X can be L, I, V, or A

<400> SEQUENCE: 3

Xaa Arg Xaa Xaa Xaa Xaa Xaa Xaa Xaa Arg Arg Trp
1               5                   10
```